United States Patent [19]
Jacober et al.

[11] Patent Number: 5,657,753
[45] Date of Patent: Aug. 19, 1997

[54] HOME BREAST SELF-EXAMINATION SYSTEM

[76] Inventors: Jeffrey M. Jacober, 498 Cole Ave.; Fran Z. Slutsky, 309 President Ave., both of Providence, R.I. 02906

[21] Appl. No.: 581,315

[22] Filed: Dec. 29, 1995

[51] Int. Cl.⁶ .................. A61B 5/00; A61B 10/00
[52] U.S. Cl. ........................... 128/630; 128/738
[58] Field of Search ................... 128/630, 738; 364/413.12; D19/20, 21, 25

[56] References Cited

U.S. PATENT DOCUMENTS

| | | |
|---|---|---|
| 3,966,161 | 6/1976 | Nichols ..................... D19/20 |
| 4,047,309 | 9/1977 | Royko . |
| 4,159,129 | 6/1979 | Lockhart . |
| 4,213,520 | 7/1980 | Sarna et al. . |
| 4,346,697 | 8/1982 | Cohen . |
| 4,367,527 | 1/1983 | Desjacques ................ 128/738 |
| 4,389,782 | 6/1983 | Webster . |
| 4,527,906 | 7/1985 | Jezbera ..................... 368/107 |
| 4,632,570 | 12/1986 | Kelsey . |
| 4,768,176 | 8/1988 | Kehr et al. . |
| 4,858,207 | 8/1989 | Buchner . |
| 4,905,213 | 2/1990 | Masse et al. . |
| 4,932,682 | 6/1990 | Miller . |
| 5,188,563 | 2/1993 | Hanauer . |
| 5,352,155 | 10/1994 | Fahey . |
| 5,365,496 | 11/1994 | Tolan-Samilow . |
| 5,515,344 | 5/1996 | Ng ........................... 128/738 |

Primary Examiner—Lee S. Cohen
Assistant Examiner—Rosiland Kearney
Attorney, Agent, or Firm—Lockwood, Alex, Fitzgibbon & Cummings

[57] ABSTRACT

A system is provided for encouraging proper timing compliance with breast examination guidelines that breast examination be conducted at a given time within the menstrual cycle of the user, typically a set number of days after onset of the menstrual cycle. A device is included which provides prompt signals at the appropriate timing during each cycle and which prompt persists until compliance is indicated. Provision is made for adjusting the cycle to comply with the expected length of the menstrual cycle of the particular woman and in order to adjust same to account for irregularities in menstrual cycles for each specific woman.

24 Claims, 2 Drawing Sheets

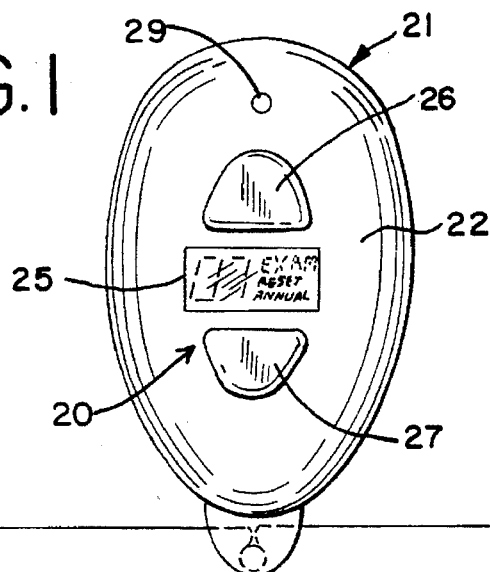
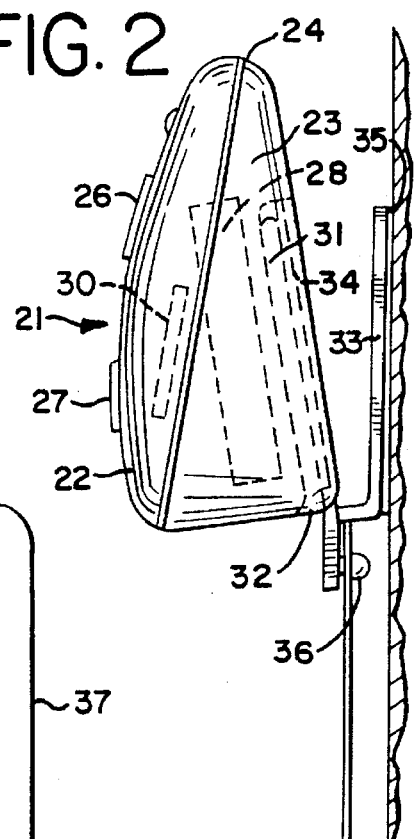
FIG. 1  FIG. 2
BREAST SELF-EXAMINATION
SHOWER CARD
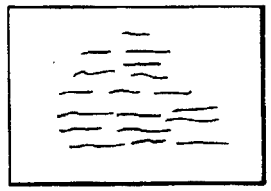 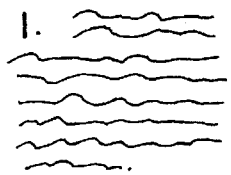
1.
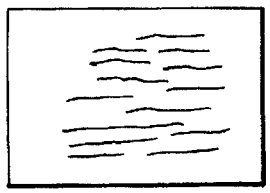 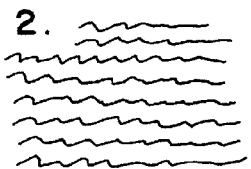
2.
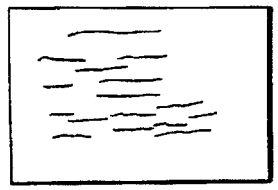 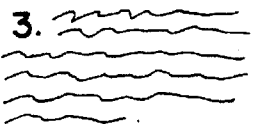
3.
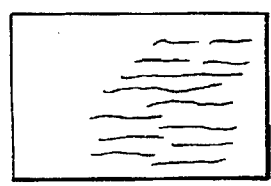 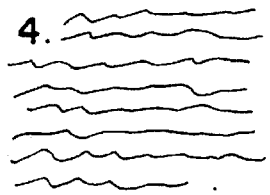
4.

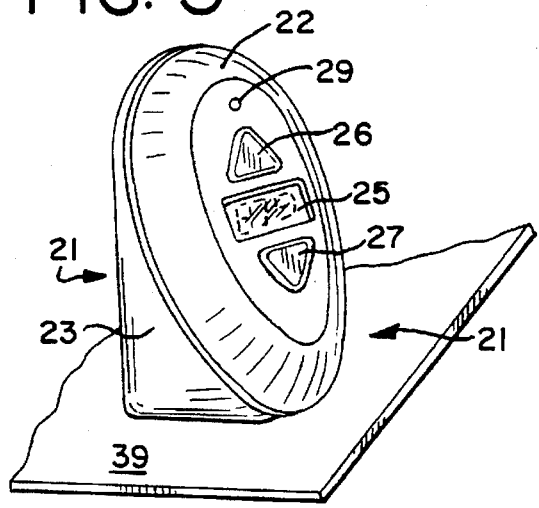
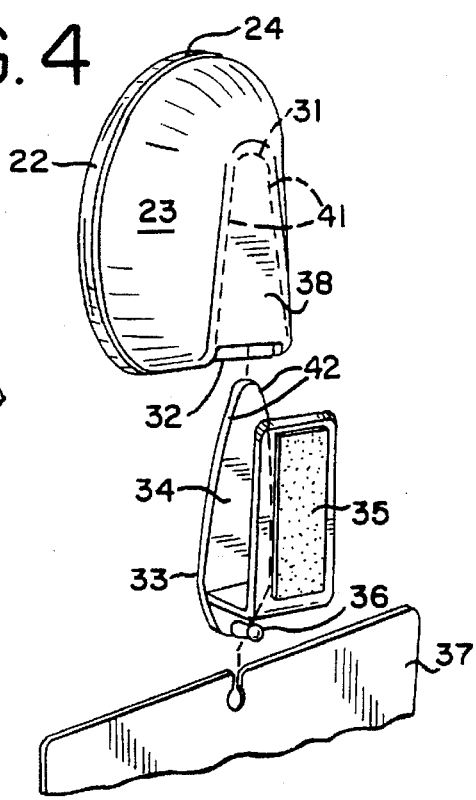
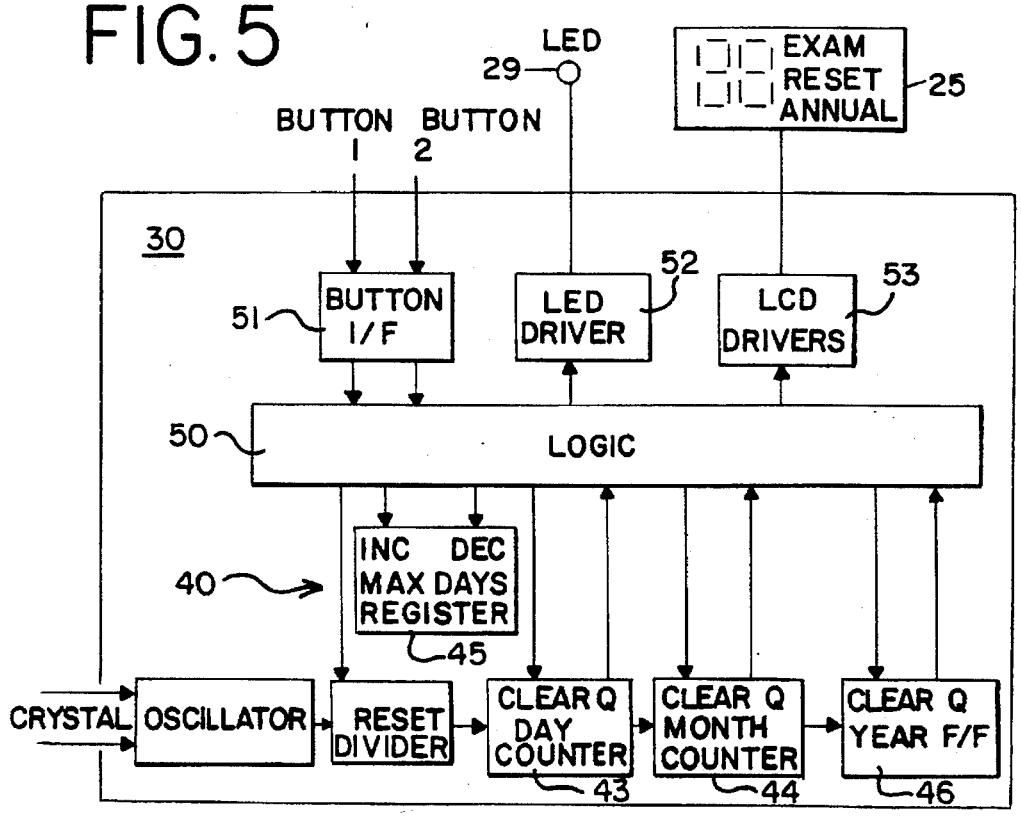

HOME BREAST SELF-EXAMINATION SYSTEM

BACKGROUND AND DESCRIPTION OF THE INVENTION

The invention generally relates to breast examination systems of the type that are suitable for in-home use on a self-examination basis. More particularly, the present invention relates to an improved device and method suitable for breast self-examination and in-home use which prompts breast self-examination on a timely basis, that is after a specified number of days from the onset of the menstrual cycle of the user. Arrangements are also provided for compensating for different and/or irregular menstrual cycle periods.

Various organizations such as the American Cancer Society, health maintenance organizations, participating provider organizations, medical societies and other health awareness organizations strongly encourage compliance with timely breast self-examination practices. It is generally believed that the most opportune time for detecting variations in normal nodularity for each woman is a given number of days after the onset of each menstrual period. Conducting the examination at a consistent time during the menstrual cycle is desirable from the point of view of carrying out the needed observations at about the same time during each menstrual period. Furthermore, it is believed to be desirable to have this timing substantially coincide with approximately seven to ten days after the onset of each menstrual cycle. In this way, any changes from base line observations of lumps, thickenings, dimpling, changes in skin texture, changes in skin color, discharges or variations from base line indicia will be subject to scrutiny at an optimal and consistent time during each menstrual cycle.

In the past, the achieving of these desirable objectives has had to rely upon the memory and self-awareness of each individual woman. For most women, the desirable timing discussed herein is not achieved by simply conducting the breast self-examination on a given date of each calendar month. Accordingly, a system is needed which will aggressively prompt breast self-examination at a given time during each menstrual cycle, irrespective of the calendar date. Furthermore, such a system should be versatile enough to allow for variations in the length of menstrual cycles from woman to woman and, in many instances, from cycle to cycle of the same woman.

Additionally, a primary opportunity for many stages of breast self-examination is while bathing, such as during the course of daily showering or the like. In order to take advantage of this opportune timing, it is desirable that the breast self-examination timing and reminder device be capable of being on-display within the user's shower stall, for example.

It has been found that, by proceeding in accordance with the present invention, it is possible to provide persistent prompts, which are timely in the sense that is discussed herein, for breast self-examination. This timeliness is capable of being tailored to the menstrual cycle pattern, whether regular or irregular, of each individual woman.

SUMMARY OF THE INVENTION

In summary, the present invention is a system, device and method for in-home breast self-examination. Operational circuitry is included within a compartment having a display panel and a control assembly. In the preferred arrangement, this compartment is sealed to the extent that it is water-resistant and capable of being positioned within a shower stall or the like. The operational circuitry has timing data channel circuitry which times a sequential count of 24-hour days which are designated between day 01 and a selected end day number. This circuitry also repeats such a sequential count. Message data channel circuitry initiates a persistent prompt message at the display panel when a preselected intermediate day number is reached by the timing data channel circuitry. This intermediate day number corresponds to a set number of days after onset of the menstrual cycle of the user, an exemplary such set number being seven days. In response to the prompt message, the user conducts a breast examination and activates a compliance control of the control assembly, thereby cancelling the prompt message from the display panel. The timing data channel circuitry continues to count off days until the day number 01 is again displayed. This procedure is repeated during each menstrual cycle of the woman. The invention allows for personalization of the sequential count timing; preferably reset data channel circuitry is included for resetting the sequential count of days to day 01 in response to the onset of the menstrual cycle of the particular woman. In addition, the invention can preferably include the ability to vary the designated end day number in order to better correspond to a typical menstrual cycle length of the particular woman for whom the device is to be used.

It is a general object of the present invention to provide an improved system, device and method for breast self-examination which is especially suitable for in-home use.

Another object of the present invention is to provide an improved breast examination system that has the capability of being tailored to the specific needs of the individual woman who is to use the device.

Another object of this invention is to provide an improved home breast self-examination system, device and method which is usable within shower stalls and the like in order to provide reminder and prompting information at a convenient and advantageous location.

Another object of the present invention is to provide an improved device for facilitating compliance with health professional guidelines for examination for irregularities in breast nodularity, appearance and condition.

Another object of the present invention is to provide an improved breast self-examination system and device having a reset feature for accommodating variations in a woman's menstrual cycle from month to month.

Another object of the present invention is to provide a breast self-examination device which is readily mountable at a location such as within a shower compartment and which also is suitable for table storage and display.

These and other objects, features and advantages of the invention will be clearly understood through a consideration of the following detailed description.

BRIEF DESCRIPTION OF THE DRAWINGS

In the course of this description, reference will be made to the attached drawings, wherein:

FIG. 1 is an front elevational view of a breast self-examination device in accordance with the present invention shown in association with an instruction card for breast self-examination;

FIG. 2 is a side elevational view of the arrangement illustrated in FIG. 1, illustrating the assembly as suspended from a wall, such as the wall of a shower;

FIG. 3 is a perspective view of a device in accordance with the present invention shown in an orientation for table storage and display;

FIG. 4 is a rear, exploded perspective view of an assembly as generally illustrated in FIG. 2; and FIG. 5 is a schematic illustration of the operational circuitry of a device in accordance with the present invention.

DESCRIPTION OF THE PARTICULAR EMBODIMENTS

A preferred device suitable for prompting breast self-examination is illustrated in FIGS. 1, 2, 3 and 4. This device is generally designated by reference numeral 21. In the illustrated embodiment, a water-resistant compartment includes a front panel 22 and a rear panel 23 which are suitably joined together in sealed fashion with the aid of a gasket 24. The front panel in the illustrated embodiment includes a display panel 25 and a control assembly, generally designated at 20.

The illustrated display panel can be of any suitable type, such as a liquid crystal display (LCD) of a type well-known in the art. The illustrated control assembly includes two push buttons or activation pads 26 and 27. In the illustrative embodiment that is specified herein, activation pad 26 is identified as the OKAY control, while activation pad 27 is indicated as the RESET control.

Display panel 25 and the control assembly components are suitably and controllably interconnected with operational circuitry (FIG. 5) which can be provided according to suitable technology, such as a circuitry chip and the like in a manner well-known in the art. A suitable power source is also provided, such as the illustrated dry cell battery 28 which is removably mounted within the compartment defined between the front panel 22 and the rear panel 23.

In a preferred arrangement, a signal light or display 29, such as the illustrated LED light, is sealably positioned along the front panel of the device. In the preferred embodiment as illustrated, the rear panel includes an access slot 31, the opening 32 of which is generally downwardly facing in the embodiment which is illustrated.

A holder 33 is designed to be closely and advantageously received within the access slot 31. Holder 33 includes an insertion panel 34 which preferably has a perimeter shape that is complementary to the perimeter shape of the access slot 31. It will be noted that, in the illustrated embodiment, the profile of these perimeter shapes is roughly triangular, with complimentary tapered sides 41, 42, in order to provide secure and true intermeshing engagement between the insertion panel 34 of the holder and the access slot 31 of the compartment casing of the breast self-examination device. Preferably, holder 33 also includes a mounting panel 35, which can be adhesive-based as illustrated in FIG. 4. Holder 33 also preferably includes a suspension post 36 or the like for conveniently mounting a breast self-examination shower card 37 as illustrated or other similar instruction display component. The illustrated shower card includes illustrations and text for instructing proper breast self-examination techniques. Generally speaking, the content of such cards 27 is generally known in the art, such as guidelines laid down by the American Cancer Society.

As generally illustrated in FIG. 4, access slot 31 can be formed between a depression in the rear panel 23 and a plate 38 which snaps or is glued in place. It will be appreciated that, by suitable molding techniques and devices, access slot 31 can be molded into the back panel 23, for example.

It will be noted that FIG. 3 illustrates that the device will advantageously rest on a table top 39 or the like. The noted orientation of the device 21 is such that the display panel 25 and other features of the device are readily visible when so displayed on the table.

Reference is now made to the schematic presentation in FIG. 5, illustrating the operational circuitry and the chip 30 in a schematic manner. The items present on the face of the device are generally illustrated. These include the display panel 25, the signalling display 29, as well as illustrated button 1 and button 2, which generally correspond to the actuation pads 26 and 27, respectively. Each of these is associated with suitable interfaces or drivers which interact with the logic source in a generally known manner. Timing data channel circuitry, generally designated at 40, is also provided as illustrated. Included are components for the reset function and for the function to adjust the maximum day feature, as well as for the annual functions, as discussed in greater detail herein. Each counter has a plurality of outputs Q and "clear" capabilities in accordance with generally known practices.

With further reference to the operational features of the device, the timing data channel circuitry 40 includes a logic circuit 50 and customary message data channel circuitry which interfaces with the button interface 51, the LED driver 52 and the LCD drivers 53, and the cycle of the device is started by having 01 displayed at the display panel 25. Initially, this is accomplished by connecting the device to a power source, such as by inserting a dry cell battery into the compartment. Returning to this initial stage also can be accomplished by other approaches such as use of the RESET actuation pad or button 27.

Thereafter, the timing circuit, including day counter 43, counts off 24 hours, at which time the 01 display changes to an 02 display at panel 25. Increasing day numbers are thusly generated and displayed. This proceeds until, in association with month counter 44, the designated end number of days is reached, for example day 30, or until other events occur as discussed herein.

At a preselected intermediate day, typically day 07 or day 08 or day 09 or day 10, for example, the EXAM display appears on the display panel 25. In an especially preferred arrangement, this preselected intermediate day number is day 07. In the preferred arrangement that is illustrated, the signal light or display 29 is also activated, typically taking the form of a flashing light, such as a flashing red light. These are the signals for the user to conduct the breast examination and thus be in compliance with the guidelines of medical professionals. At this stage, the user activates the compliance control, illustrated as OKAY pad or button, such as at 26, at which time the EXAM display ceases, and the attention light 29 is no longer lit and ceases flashing.

In the event that the user is not in compliance and does not activate the OKAY pad, the following occurs after 24 hours after reaching the preselected intermediate day (i.e. day 08 when day 07 is the preselected intermediate day). The attention display or light 29 ceases flashing and is no longer illuminated. This is done in order to minimize power drain. In addition, the EXAM display of the display panel 25 remains visible and advances to a flashing mode. This mode continues until the OKAY pad is activated, for example. By this approach, the device provides a persistent reminder for the user to achieve compliance.

As previously mentioned, the timing cycle continues to count off and display the number of days since initiation, which corresponds to the onset of the menstrual cycle of the user. This counting continues until day 30 is reached, which is in accordance with the default mode of the counter. If the menstrual cycle of the woman is consistently 30 days, then there is no need to adjust this default value. If the woman's cycle is generally greater than or less than 30 days, the default cycle can be set to a different number of days. In this illustrated embodiment, changing of the length of this cycle is accomplished with the use of the "Max Days Register" 45 in the following manner. Both the RESET and the OKAY pads or buttons are activated and held together in their activated state, at which time the display panel 25 shows the default cycle time, for example 30 for thirty days. Activating the RESET pad once causes the cycle time of the register 45 to count upward by one, for example from 30 to 31. Continued activation of the RESET pad changes its setting upwardly at high speed. Similarly, by activating the OKAY pad once, the cycle time of the register 45 counts downward by one, for example from 30 to 29. Again, continued activation of the OKAY pad changes its setting at high speed. Once the desired cycle time is set, the number display will revert back to 01 about 15 seconds after activation of the RESET and/or OKAY pads.

For those situations where the woman's menstrual cycle does not follow the thus set number of days, the following can be accomplished in order to nevertheless achieve the proper compliance timing. If the menstrual cycle period is shorter or longer than that of the designated end day number to which register 45 of the device is at default or had been set, proper timing adjustment can be accomplished by way of the reset function. More specifically, the user activates the RESET pad once, at which time the word RESET appears on the display panel 25 and blinks. This blinking continues for about 15 seconds, and the display will simply cease if the RESET pad is not further activated during that time period. A second activation of the RESET pad during this blinking phase will cycle the day number back to 01, which will be visible on the display panel 25. Thus, in the instance where the "default" 30 day value is sequenced into the device, and when the woman's menstrual cycle had a duration of only 28 days, proceeding through this RESET mode will change the display from 28 to 01. In those instances where the woman's menstrual cycle is greater than 30 days in this example, the count on the display panel already would have begun at the beginning of the timing cycle; for example, when the woman's menstrual period was 33 days, an 03 will be displayed, and activation of the RESET function as described will change the 03 to 01.

In an optional arrangement, the activation of the RESET function will also delete the EXAM display, whether constant or blinking, and will also cease activation of the signal display 29 if same is still activated. This occurs, of course, in those instances where the menstrual cycle lasted to or beyond the designated intermediate day number, for example 07.

The counting circuit includes a yearly function, including Year F/F circuit 46, in order to prompt the user to proceed with an annual checkup with a medical professional or organization. The word ANNUAL appears on the display panel 25 on day 01 of typically the thirteenth cycle. In addition, in the illustrated embodiment, the display alert member 29 is illuminated and begins to flash. Flashing continues for 24 hours and ceases thereafter in order to conserve available power. The ANNUAL display persists, but the device otherwise locks up. That is, the device stops working or counting and does not respond to activation of the control assembly, such as the OKAY pad and/or the RESET pad. This locked up condition persists until the power supply is replenished, such as by inserting a new dry cell battery into the device. Thus, with this feature, the user has been prompted to obtain a desired annual health professional checkup to assess any changes in breast nodulation and appearance from the base line information. At the same time, there is assurance that the device will not fail during the coming year due to a power source that is not adequate for the entirety of the coming year.

As previously mentioned, the device is water-resistant, typically up to a water depth of about 1 inch. The device is also readily portable and easily fits into a purse or the like. Generally speaking, the device has a maximum width of about 5 cm (approximately 2 inches), a maximum height of about 8 cm (approximately 3 inches), a maximum depth of about 4.5 cm (approximately 1.75 inches), and a depth at its narrowest location of about 2 cm (approximately 0.8 inch). The illustrated embodiment will operate on a single AA size dry cell battery.

It will be understood that the embodiments of the present invention which have been described are illustrative of some of the applications of the principles of the present invention. Various modifications may be made by those skilled in the art without departing from the true spirit and scope of the invention.

I claim:

1. A device for prompting compliance with timely breast self-examination, comprising:
    a water-resistant compartment having a display panel and a control assembly;
    operational circuitry that is self-contained with respect to said water-resistant compartment and that is in data-passing communication with said display panel and with said control assembly;
    said operational circuitry including timing data channel circuitry for timing a sequential count of 24-hour days from day 01 until a designated end day number is reached and for repeating said sequential count once said designated end number is reached, and said display panel displays said days from 01 to said designated end number;
    said operational circuitry further including message data channel circuitry associated with said timing data channel circuitry for initiating a prompt message at said display panel when a preselected intermediate day number is reached by said timing data channel circuitry, said intermediate day number being between 01 and said designated end day number, and said intermediate day number corresponds to a set number of days after onset of the menstrual cycle of the user;
    said control assembly has a compliance control which, when activated, deletes said prompt message from said display panel and thus inputs to said operational circuitry a signal of compliance with timely breast self-examination; and
    said operational circuitry includes reset data channel circuitry for resetting said sequential count in response to the onset of the next menstrual cycle of the user when same does not correspond to the designated first day number of the sequential count.

2. The device in accordance with claim 1, wherein said reset data channel circuitry resets said sequential count of days to day 01 when a reset pad is activated.

3. The device in accordance with claim 1, wherein said prompt message displays a word message at said display panel.

4. The device in accordance with claim 1, wherein said prompt message includes a flashing light mounted on the water-resistant compartment.

5. The device in accordance with claim 1, wherein said prompt message includes a word message display that changes to an intermittent word message display after a given time period.

6. The device in accordance with claim 1, wherein said prompt message includes a word message display and a flashing signal which persist for a given period of time, after which the flashing signal ceases and the word message display becomes an intermittent word message display.

7. The device in accordance with claim 5, wherein the given time period is about one day.

8. The device in accordance with claim 1, further including data channel circuitry for adjusting the designated end day number in order to either incrementally increase same or incrementally decrease same.

9. The device in accordance with claim 8, wherein the time period for said incremental increase or decrease is about one day.

10. The device in accordance with claim 1, wherein said timing data channel circuitry further includes an annual function that occurs at the beginning of a chosen sequential count to thereby provide a generally annual prompt.

11. The device in accordance with claim 10, wherein said generally annual prompt includes a message display and stopping of all other functions of the device.

12. The device in accordance with claim 1, further including a holder for supporting the device on a vertical surface.

13. The device in accordance with claim 12, wherein said compartment includes an access slot, and wherein said holder has an insertion panel that fits into the access slot in order to thereby support and display the device when the holder is secured to a vertical surface such as a wall of a bathing area or the like.

14. The device in accordance with claim 13, wherein said access slot includes tapered sides by virtue of which said access slot reduces in width in an upward direction, and wherein said insertion panel has tapered sides which are generally complementary to said tapered sides of the access slot, said respective tapered sides of the access slot and of the insertion panel being in intermeshing engagement when said device is supported by the holder.

15. The device in accordance with claim 1, wherein said compartment is self-supporting in an upward orientation when the device is resting on a horizontal surface.

16. A method for compliance with timely breast self-examinations, comprising the steps of:
providing a device having a water-resistant compartment with a display panel, a control assembly and operational circuitry with timing data channel circuitry for timing sequential counts of days from day 01 to a designated end day number and for repeating said sequential count, said display panel displaying the day number generated by the timing data channel circuitry, the operational circuitry further having message data channel circuitry for initiating a prompt message at the display panel when a preselected intermediate day number is reached by said timing data channel circuitry, said preselected intermediate day number being a specified number of days after the onset of the menstrual period of the user, and said control assembly includes a compliance control;
setting said day number to 01 in correspondence with the onset of the menstrual cycle of the user;
conducting a breast examination of the user in response to the prompt message shown at the display panel of the device at the preselected intermediate day number;
activating the compliance control of the control assembly to cancel the prompt message from the display panel;
allowing the timing data channel circuitry to continue until the 01 day number is again displayed at the display panel; and
repeating said conducting, activating and allowing steps so as to effect the breast examination a plurality of times on said preselected intermediate day number.

17. The method in accordance with claim 16, wherein said data channel circuitry further includes reset data channel circuitry and the method further includes the step of resetting a value of the sequential count of days to 01 to designate onset of the next menstrual cycle of the user.

18. The method in accordance with claim 16, wherein said designated number of days is between about 7 and about 10.

19. The method in accordance with claim 16, wherein said prompt message displays a word message at said display panel.

20. The method in accordance with claim 16, wherein said prompt message includes a flashing light mounted on the water-resistant compartment.

21. The method in accordance with claim 16, wherein said prompt message includes a word message display that changes to an intermittent word message display after a given time period.

22. The method in accordance with claim 16, wherein said prompt message includes a word message display and a flashing signal which persist for a given period of time, after which the flashing signal ceases and the word message display becomes an intermittent word message display.

23. The method in accordance with claim 16, wherein said data channel circuitry further adjusts the designated end day number and the method includes either incrementally increasing or incrementally decreasing the designated end day number.

24. The method in accordance with claim 23, wherein the time period for said incremental increase or decrease is about one day.

* * * * *